United States Patent [19]

Cahill et al.

[11] Patent Number: 5,428,696
[45] Date of Patent: Jun. 27, 1995

[54] PHOTOMETRIC INSTRUMENT WITH OPTICAL FIBERS FOR ANALYZING REMOTE SAMPLES

[75] Inventors: Jerry E. Cahill, Trumbull; David H. Tracy, Norwalk, both of Conn.

[73] Assignee: The Perkin-Elmer Corporation, Norwalk, Conn.

[21] Appl. No.: 92,162

[22] Filed: Jul. 15, 1993

[51] Int. Cl.6 .............................................. G02B 6/26
[52] U.S. Cl. ......................................... 385/16; 385/17; 385/20; 385/25
[58] Field of Search ..................... 385/12, 15, 16, 17, 385/20, 25, 59

[56] References Cited

U.S. PATENT DOCUMENTS

| | | | |
|---|---|---|---|
| 3,519,116 | 7/1970 | Koehn | 385/21 X |
| 4,239,330 | 12/1980 | Ashkin et al. | 385/21 X |
| 4,261,638 | 4/1981 | Wagner | 385/25 |
| 4,378,144 | 3/1983 | Duck et al. | 385/16 |
| 4,431,307 | 2/1984 | Suovaniemi | 356/246 |
| 4,589,726 | 5/1986 | Buhrer | 385/21 |
| 4,626,065 | 12/1986 | Mori | 350/96.15 |
| 4,650,277 | 3/1987 | Husher et al. | 385/33 X |
| 4,789,215 | 12/1988 | Anderson et al. | 385/18 |
| 4,886,356 | 12/1989 | Paradis | 356/246 |
| 4,968,148 | 11/1990 | Chow et al. | 356/427 |
| 4,989,932 | 2/1991 | Landa et al. | 350/96.1 |
| 5,056,886 | 10/1991 | Hoult | 385/20 |
| 5,077,481 | 12/1991 | Hoult | 250/573 |
| 5,147,348 | 9/1992 | Leckrone et al. | 385/90 X |
| 5,170,446 | 12/1992 | Sullivan et al. | 385/19 |

FOREIGN PATENT DOCUMENTS

| | | | |
|---|---|---|---|
| 83/00384 | 2/1983 | WIPO | G01J 33/50 |
| 92/10737 | 6/1992 | WIPO | G01N 21/01 |

Primary Examiner—Frank Gonzalez
Attorney, Agent, or Firm—Edwin T. Grimes; Herbert S. Ingham

[57] ABSTRACT

In a spectrophotometer, each of a plurality of source optical fibers is selectively receptive of source radiation and carries the radiation to a corresponding selected liquid sample cell. A corresponding return optical fiber returns transmitted radiation from the sample to a polychromator. For selecting a sample, a switching member holds exposed ends of the optical fibers on a circle coaxial with an axle for rotating to selected positions. Respective optical trains in the instrument direct radiation into and out of the selected pair of fibers. The diameter of a source aperture, the spacing of the aperture from the radiation source, and the source area define a source etendue. The optical fibers have a fiber etendue substantially the same as the source etendue.

18 Claims, 4 Drawing Sheets

PHOTOMETRIC INSTRUMENT WITH OPTICAL FIBERS FOR ANALYZING REMOTE SAMPLES

This invention relates generally to photometric instruments such as spectrophotometers, and particularly to such instruments that analyze transmittance properties of a plurality of samples. The invention also relates to the utilization of optical fibers and optical switching in such instruments.

BACKGROUND OF THE INVENTION

A variety of photometric instruments are used for analyzing radiation transmitted or reflected by samples, in order to ascertain the nature of the sample. Spectrophotometers, in particular, are used to provide a spectrographic analysis, for example to determine the existence or concentration of components in a sample, or to provide a "fingerprint" spectrum characteristic of a sample. A typical application is measurement of dissolution rate of a pharmaceutical tablet in a solution, whereby changes in light transmission through the solution are monitored over time. Another type of instrument is used in liquid chromatography in which a sample solute is injected into a flowing solvent while transmitted radiation is monitored.

A conventional class of spectrophotometers is utilized for measuring optical transmission of liquid samples in a spectral range from infrared to ultraviolet. Usually a sample cell for liquid, also known as a "cuvette", such as described in U.S. Pat. No. 4,886,356 (Paradis), is incorporated into the instrument with the liquid being placed in or pumped through the cuvette chamber. Recently optical fibers have been adopted to carry radiation to a cuvette or probe remote from the instrument. In such case a probe may be designed to be immersed in the liquid as described, for example, in U.S. Pat. No. 5,077,481 (Hoult).

It sometimes is desirable to monitor several samples at once, for example for different tablets dissolving in a number of containers over the same period of time. U.S. Pat. No. 4,431,307 (Suovanieme) teaches arranging liquid containers in a matrix, with each container being self contained with its own optics and detector as a simple photometer. Alternatively, a single instrument with one pair of optical fibers can be used to convey radiation to and from a group of cuvettes or probes where optical switching selects the sample being analyzed, for example as disclosed in U.S. Pat. No. 4,968,148 (Chow et al). Switching for optical fibers generally is directed to rerouting radiation from one fiber (or group of fibers) to another fiber (or group of fibers); examples of this type of switching are disclosed in U.S. Pat. Nos. 5,056,886 (Hoult) and 4,626,065 (Mori).

When a single pair of optical fibers convey radiation continuously to and from a single cuvette or probe, or an array of cuvettes, the fibers may deteriorate significantly by extended exposure to the radiation. This particularly occurs in the UV range where the phenomenon is known as solarization.

U.S. Pat. No. 4,989,932 (Landa et al) discloses a multiplexer which enables light to be sent to and received from samples selectively for analysis. A rotatable barrel containing a pair of angled mirrors is placed axially in a light path. One mirror deflects light transversely to an optical fiber which conveys the light to a sample. Another fiber returns light from the sample to the other mirror which deflects the light back along the original path. The barrel is rotated on the axis to select from different pairs of optical fibers which extend in various radial directions. Although a stepper motor is suggested for rotating the barrel, no mechanism is shown for support or rotation in the optical path. Also, precise alignment is necessary for the rotatable mirrors and fibers relative to the path.

An object of the present invention is to provide a means for optimizing optical coupling between a photometric instrument and one or more external samples through the use of optical fibers, particularly for liquid transmittance samples. Another object is to provide such an instrument with a means for switching among many pairs of optical fibers in a limited space. A further objective is to provide such an instrument with a high degree of repeatability between measurement cycles. Yet another objective is to provide such an instrument with a system of optical fibers so that solarization of any one fiber is substantially reduced.

SUMMARY OF THE INVENTION

Foregoing and other objects are achieved at least in part with a selection apparatus for a photometric instrument, such as a spectrophotometer, that includes a source of radiation and means for utilizing transmitted radiation. The selection apparatus comprises a plurality of source optical fibers each being selectively receptive of radiation from the source. The apparatus further comprises a corresponding plurality of return optical fibers, a corresponding plurality of sample means each being disposed for a sample therein, such as a liquid, to transmit radiation from a corresponding source fiber to a corresponding return fiber, and a switching means.

The switching means selectively directs source radiation into a selected source fiber, and directs transmitted radiation from a correspondingly selected return fiber to the utilization means. The switching means comprises a retaining member with an axis, and a positioner operatively connected to the retaining member for selectively positioning the retaining member rotationally about the axis. The retaining member retains an exposed end of each of the optical fibers, each exposed end being located on a circle coaxial with the axis. The source fibers are paired with the return fibers, advantageously diametrically oppositely, so that for each selected position of the retaining member, a correspondingly selected source fiber is aligned so its exposed end is receptive of source radiation and a correspondingly selected return fiber is aligned so its exposed end directs transmitted radiation to the utilization means.

Objects are further achieved with a radiation source having a source area, and a source aperture having an aperture area with spacing from the source, so as to define a source etendue. Radiation is passed by the source aperture into an optical fiber that has a fiber etendue substantially the same as the source etendue.

In a further aspect, the source area and the source aperture constitute an aperture pair consisting of a first aperture and a second aperture. An input optical train is disposed to direct passed radiation through an exposed input end of the selected source fiber. A first focusing means such as a concave mirror focuses the first aperture to an aperture image at an image plane. A second focusing means such as a lens has a focal plane located at the image plane and is disposed so that the aperture image is focused at infinity through the input end into the selected source fiber. The lens also focuses an image of the second aperture on the input end. Preferably, an output optical train is disposed with respect to the analyzer means to direct transmitted radiation from an exposed output end of the correspondingly selected output fiber. An output train is configured substantially the same as the input optical train.

DETAILED DESCRIPTION OF THE INVENTION

The present invention may be utilized with essentially any photometric instrument, particularly an absorption spectrophotometer, in which a beam of light radiation (visible, near-infrared, infrared or ultraviolet) is to be deflected from the instrument to a sample and returned by way of fiber optics.

Figure 1:
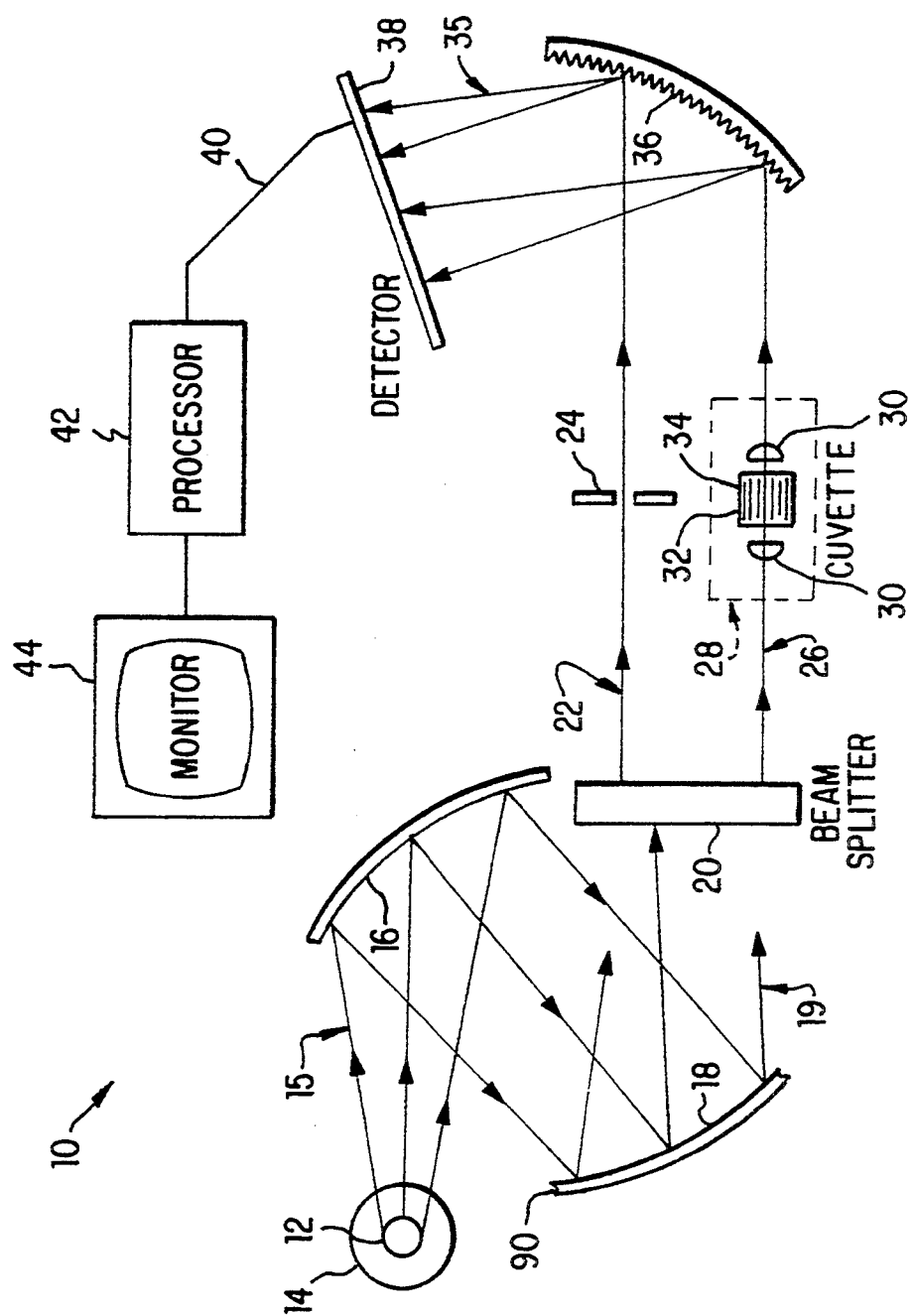
FIG. 1 is a schematic diagram of a conventional spectrophotometer useful for incorporating the invention.

A conventional instrument 10 suitable for the invention, such as a model LC-235 sold by The Perkin-Elmer Corporation, is shown schematically in FIG. 1. A deuterium arc light source 12 in a quartz tube 14 emits radiation 15 in the ultraviolet (UV) range. A first concave mirror 16 collimates radiation to a second concave mirror 18 which passes a portion 19 of the radiation and converges the beam toward a beam splitter 20. In some cases only one concave mirror, or a lens system, may be used to effect the converging beam. Additionally, planar mirrors (not shown) may be used for folding the beam, but these are not relevant to the invention.

The beam splitter 20 divides the original beam 15 into two beams of radiation. One beam 22 is a reference beam passed through an aperture 24. The other beam 26 is directed through a cuvette 28 typically having a pair of lenses 30 on either side of a sample cell 32 in which a liquid 34 is placed or flowed through for analysis. Both beams are dispersed spectrally 35 by a polychromator with a concave grating 36 and focused onto an array detector 38 which provides corresponding signals on a line 40 to a programmed processor 42. In practice the grating 36 and the detector 38 are rotated so that the detector is 90° out of the FIG. 1 diagram. The processor processes the signals, for example comparing spectral data for the sample beam with that of the reference beam, to produce output information for display by a monitor 44 or printer.

According to the invention, the cuvette 32 in the instrument is replaced with an optical apparatus 46 (FIG. 2) incorporating fiber optics. The rest of the instrument may be substantially the same as for FIG. 1, but is simplified in FIG. 2 for clarity. For example, the beam splitter and the parallel reference beam are omitted but may be present as needed. Radiation 15 from the arc is passed through a source lens 48 (replacing or representing the pair of concave mirrors) which directs the passed radiation beam 26 into the substitute optical apparatus. (The term "lens" as used herein and in the claims means a single lens or a combination of lenses having a similar function.)

In an input optical train 50 of the apparatus, a planar mirror 52 deflects the converging source beam 26 through an input aperture 54 in a plate 55 and an input focusing lens 56 to an optical fiber 58, designated herein "source fiber", held at its end 60 in a retaining member 62. The input aperture alternatively may be the physical size of the source image, but preferably is an actual aperture stop 54, most preferably at the location indicated. Source radiation 26 is then carried by the fiber to a distal end 63 at a remote location 64 where a liquid (or other semitransparent) medium is to be tested. Alternatively the sample may be reflective. (As used herein and the claims, "transmit" and transmitted" include direct transmissions as well as reflection from a sample.) In the case of liquid, a conventional cuvette or probe 68, with or without associated lenses 70, has a chamber 72 for liquid 66 (or other) sample which selectively absorbs some of the radiation, thereby transmitting at least a portion of the radiation into a distal end 73 of a return fiber 74. The return fiber 74 with an end 76 held in the retaining member 62 carries the transmitted radiation back to the instrument. The cuvette or probe 68 may be any ordinary or desired type such as described in the aforementioned U.S. Pat. Nos. 4,886,356 and 5,077,481.

In an output optical train 77, an output lens 78 with a focal plane 79 at an output aperture 80 in a second stop 81, and a further deflecting mirror 82, have respective configurations and dispositions (focal length, separations and the like) relative to the end 76 of the output fiber, substantially the same as those in the optical train 50 relative to the end 60 of the fiber on the input side. The transmitted radiation 84 is thence redirected by the second mirror 82 for utilization by the grating 36 and the detector 38 in the manner of FIG. 1. Preferably a spectral image 85 of the source 12 is focused on the detector. The processor 42 processes signals for presentation to the monitor 44.

The source lens 48 (or equivalent concave mirror system) is configured and disposed to focus an image of the source arc 12 at an image plane 88 preferably located at the input aperture 54. The image plane also coincides with a focal plane of the lens 56. Moreover, the periphery 90 of the source lens 48 (or of the second concave mirror 18 of FIG. 1) constitutes an aperture for the source radiation, herein designated "source aperture". Another aperture may be substituted for this purpose, such as a separately located aperture stop or, with reference to FIG. 1, the periphery of the first mirror 16 may effect the aperture instead of the second mirror. In any case, the input lens 56 is configured and disposed to focus an image 91 (FIG. 3) of the source aperture onto the exposed end 60 of the radiation-carrying core 94 of the fiber.

Alternatively, with some ordinary rearrangement of the optics (not shown), focusing of the source 12 and the source aperture 90 may be reversed. Thus the source 12 may be focused on the fiber core 94 and the source aperture 90 would be then focused on the input aperture 54. More generally, the source area and the source aperture constitute a pair consisting of a first aperture and a second aperture, with the term "first aperture" referring to either the source area or the source aperture, and "second aperture" referring to the other. A first focusing means is disposed to focus the first aperture to a first image at an image plane. A second focusing means has an input focal plane coinciding with the image plane, and is disposed so that the first image is focused at infinity into the selected source fiber, so as to fill the numerical aperture of the fiber. The second focusing means also focuses an (viz. a second image) image of the second aperture on the input fiber end. It may seen that, in the embodiment of FIG. 2, the first aperture is the source area 96, the second aperture is the source aperture 90, the first focusing means is the lens 48, and the second focusing means is the lens 56.

Figure 2:
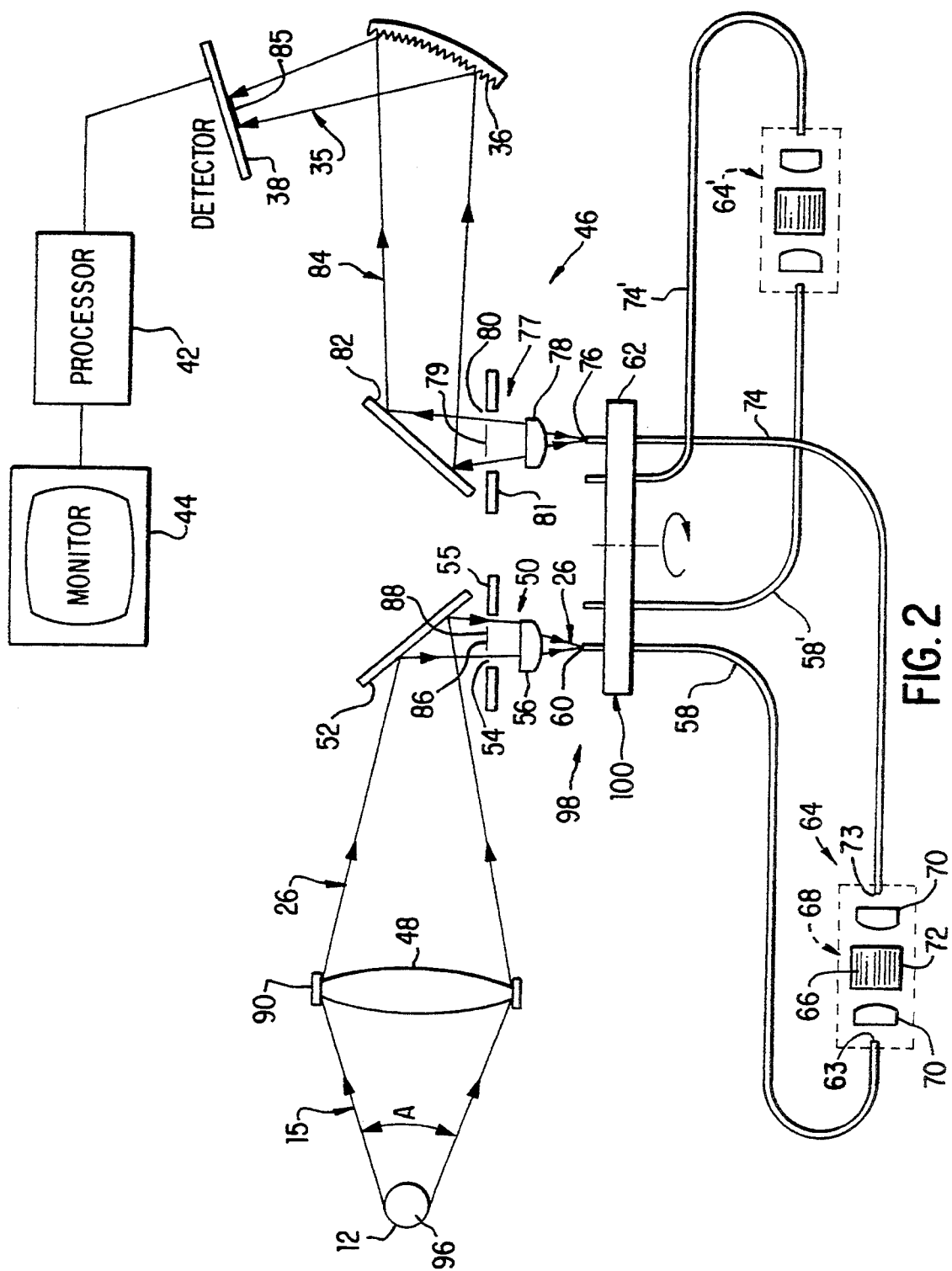
FIG. 2 is a schematic diagram of a spectrophotometer incorporating the invention.
Figure 3:
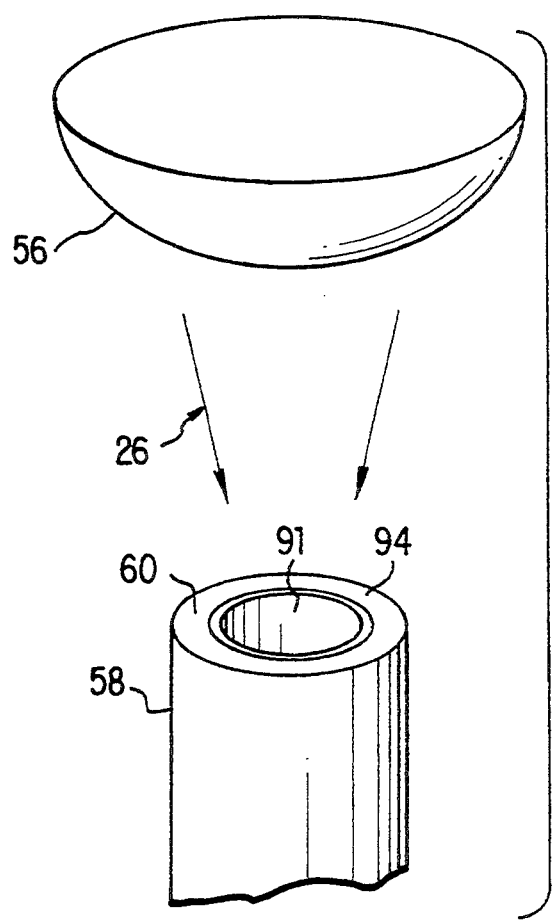
FIG. 3 is a perspective of an exposed end of an optical fiber used in the spectrophotometer of FIG. 2.

Etendue is conventionally defined as an effective area of an optical source or image multiplied by a solid angle of radiation diverging from the source or image. In the instrument of FIG. 2, the etendue for the source is the area 96 of the source multiplied by the solid angle A subtended by the source aperture. (Solid angle is the aperture area divided by separation distance squared.) In the instrument of FIG. 1, the periphery either of the first mirror 16 or preferably the second mirror 18 defines the solid angle. The etendue of an optical fiber is pi times the square of its numerical aperture (established by indexes of refraction of the core and sheath) multiplied by the cross sectional area of the core 94 (FIG. 3).

According to a preferred aspect of the present invention, the fibers all have a common etendue which is substantially the same as the source etendue. Also, the fibers should have a common numerical aperture which is substantially the same as the numerical aperture of the input train defined by the circular input aperture and the focal length of the input lens. These restrictions are provided in order to minimize losses and optimize optical couplings and spectral resolution.

It further is desirable that the size of input image 91 (FIG. 3) at the fiber core end be nominally mismatched from the cross section of the core 94. Although this results in a small radiation loss, the mismatch allows for some misalignment of the fiber with the adjacent optical train without significant loss from designed optical efficiency. It was determined that the image size should have a deviation that is within about 10% to 20% of the core size to achieve a suitable compromise. In FIG. 3 the image is shown slightly smaller than the core; it could be slightly larger.

The foregoing optical apparatus is particularly adaptable for selectively testing transmission characteristics of a plurality of samples. With further reference to FIG. 2, a selection means 98 is provided for selectively transmitting passed radiation through a selected sample to effect transmitted radiation. A plurality of source optical fibers 58, 58' (two shown) each is selectively receptive of passed radiation. There also is a corresponding plurality of return optical fibers 74, 74', and a corresponding plurality of sample means 64, 64' each being disposed to transmit radiation from a corresponding source fiber to a corresponding return fiber. A switching means 100 selects a source fiber to receive passed radiation and returns transmitted radiation from a correspondingly selected return fiber to the analyzer side of the instrument.

Figure 4:
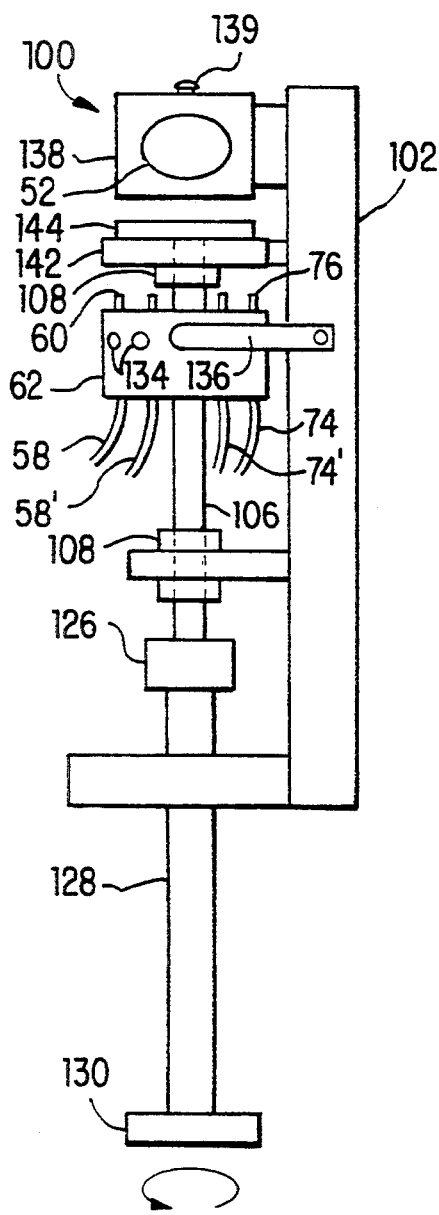
FIG. 4 is an elevation of a switching means used in the spectrophotometer of FIG. 2.

A particular optical apparatus containing a switching means 100 is shown in FIG. 4. Various components are mounted on a frame 102, one end of which fits into the spectrophotometer in place of the original coulette. The switching means includes a retaining member 62 which is cylindrical and supported by an axle 106 mounted in bearings 108 on the frame.

Figure 5A:
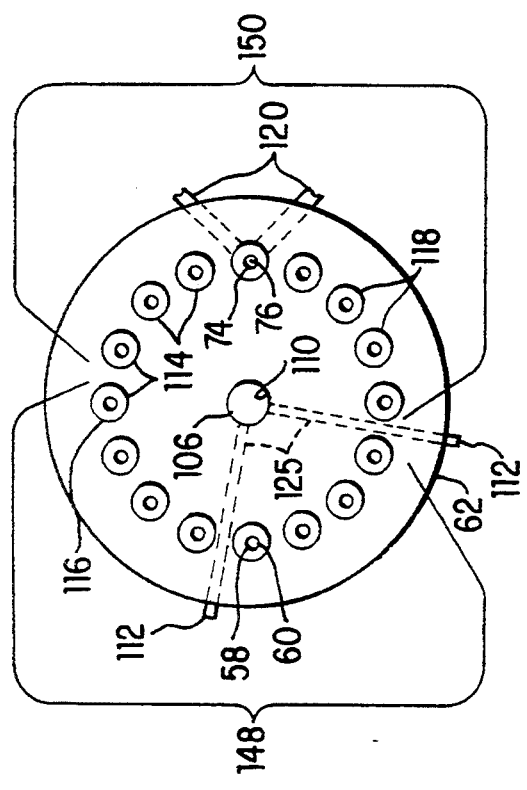
FIGS. 5a and 5b are respectively an end view and a side view in partial cross section of a retaining member for optical fibers used in the spectrophotometer of FIG. 2.
Figure 5B:
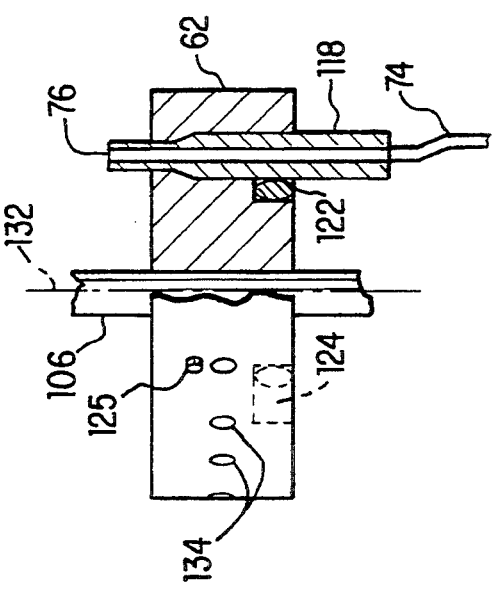

Details of the retaining member 62 with fibers 58, 58', 74, 74' are shown in FIGS. 5a and 5b. A central hole 110 contains the axle 106, with a pair of set screws 112 to affix the axle. A ring of 16 counter sunk holes 114 are equally spaced on a circle 116 coaxial with the axis. Each of 16 fibers has an exposed end (e.g. 60, 76) affixed into a standard connector ferrule 118 held in a hole. For each hole a further pair of orthogonal set screws 120 (only one pair shown) retains the ferrule against an O-ring 122 placed in the inner side of the annular groove 124 overlapping with the ring of holes 114. The screws urge the ferrules against the O-ring allowing fine adjustments of alignment of each of the fibers with the adjacent optical train.

A flexible coupling 126 (FIG. 4) on the axle 106 is connected to a shaft 128 with a handle 130 for manually rotating the retainer 62 on its axis 132 to selected positions. Flat spots 134 or depressions on the circumference of the retainer urge against a leaf spring 136 to hold the retainer at any selected rotational position. A stepper motor (not shown) could be used to position the retainer instead of the handle and leaf spring.

Figure 6:
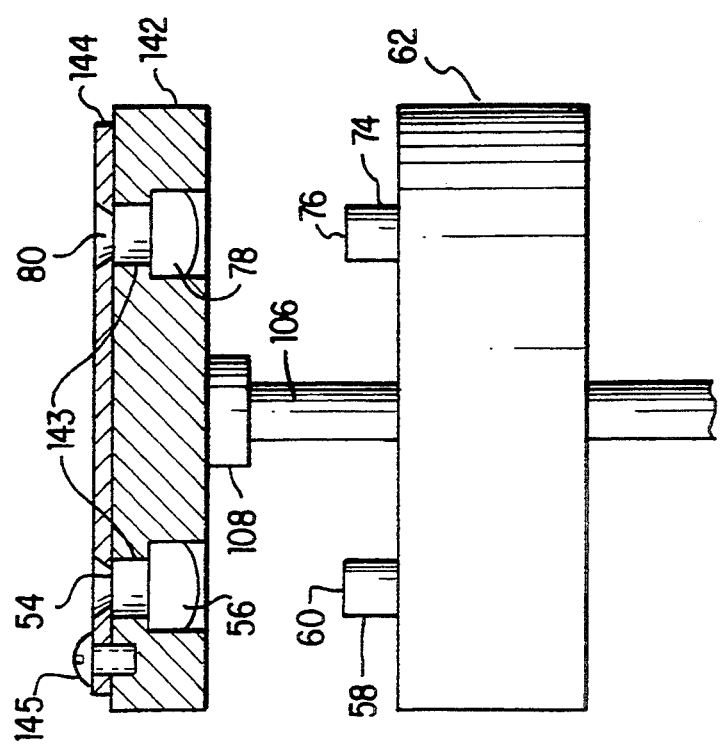
FIG. 6 is an elevation including a cross section of a holder for lenses used in the spectrophotometer of FIG. 2.

The frame also holds the input and output optical trains. A tower 138 on the frame supports the input mirror 52 which may have alignment screws 139 (one shown) and the output mirror (not seen). A disk member 142 (detailed in FIG. 6) with a pair of countersunk openings 143 supports the input lens 56 and the output lens 78 spaced from a pair of exposed fiber ends 60, 76 on the support member. A plate 144 with two apertures 54, 80 is mounted with screws 145 against the disk member so that an input aperture 54 aligns with the input lens and an output aperture 80 aligns with the output lens. The lenses could be positioned with the flat side 146 facing the fiber ends, rather than away as shown.

In the ring of fibers on the disk (FIG. 5a), eight are source fibers 148 paired against eight return fibers 150 so that, for each selected position of the retaining member, a correspondingly selected source fiber 58 is aligned with the input lens to be receptive of passed radiation, and a correspondingly selected return fiber is aligned with an output fiber 74 to return transmitted radiation to the analyzer means. Thus each pair of fibers consists of a source fiber and a return fiber having respective exposed ends located diametrically oppositely on the circle. In this example eight pairs of fibers will allow any one of eight samples to be selected for testing by the instrument. Other numbers of pairs could, of course, be embodied. One or more of the "samples" could be a blank or a standard or neat solvent, in the conventional manner.

Dimensional examples for the foregoing instrument are as follows: The first and second mirror have radii of curvature respectively of 16.6 and 25.1 cm. The second mirror has a 0.64 cm diameter aperture size. Distances are: from the arc to the first mirror, 11.2 cm; from the first mirror to the second mirror, 19.0 cm; from the second mirror to the input aperture, 8.4 cm. The input aperture has a 1.2 mm diameter, and the input lens has a 3 mm focal length. This combination of aperture diameter and focal length will focus rays at the edge of the aperture just inside the fiber numerical aperture of 0.22. The fiber core has a 0.25 mm diameter, yielding an etendue of 0.0075 $mm^2$. The source arc has diameter of 1.0 mm so that, correcting for the first mirror, the second mirror aperture size provides a source numerical aperture of 0.056 and an etendue of 0.0077 mm².

It will be appreciated that the foregoing invention provides, in addition to advantages previously indicated, a particularly useful system for a spectrometric instrument to accommodate types of fluid samples that are impractical to bring into the instrument. Such samples include those that are too large and cannot be sampled, or that require instantaneous results as in monitoring a production facility, or that cannot be transported readily such as hazardous or hot liquids. Also, the adaptations for fiber ends and switching within the instrument are relatively compact compared with provisions for handling the sample fluid in the instrument.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

We claim:

1. A selection apparatus for a photometric instrument that includes a source of radiation and utilization means for utilizing transmitted radiation, the apparatus comprising a plurality of source optical fibers each having an exposed end and a distal end, a corresponding plurality of return optical fibers each having an exposed end and a distal end, a corresponding plurality of sample means each being disposed between distal ends of a corresponding source fiber and a corresponding return fiber for a sample in the sample means to transmit radiation from the corresponding source fiber to the corresponding return fiber, and switching means for selectively directing source radiation into a selected source fiber and directing transmitted radiation from a correspondingly selected return fiber to the utilization means, wherein the switching means comprises a retaining member with an axis and further comprises positioning means operatively connected to the retaining member for selectively positioning the retaining member rotationally about the axis, the retaining member retaining an exposed end of each of the source fibers and the return fibers, each exposed end being located on a circle coaxial with the axis, and the source fibers being paired with the return fibers so that, for each selected position of the retaining member, a correspondingly selected source fiber is aligned so its exposed end is receptive of source radiation and a correspondingly selected return fiber is aligned so its exposed end directs transmitted radiation to the utilization means.

2. The apparatus of claim 1 wherein at least one sample is a liquid for transmitting the radiation.

3. The apparatus of claim 1 wherein each pair of fibers consists of a source fiber and a return fiber having respective exposed ends located diametrically oppositely on the circle.

4. The apparatus of claim 1 wherein the positioning means comprises an axle affixed axially to the retaining member, and rotation means operatively connected to the axle for rotating the axle so as to selectively position the retaining member.

5. The apparatus of claim 1 wherein the source has a circular source area, the instrument further includes a source aperture with an aperture area with a spacing from the source so as to define a source etendue, and the fibers have a common fiber etendue substantially the same as the source etendue.

6. The apparatus of claim 5 wherein the source area and the source aperture constitute an aperture pair consisting of a first aperture and a second aperture, the apparatus further comprises an input optical train disposed with respect to the source to direct passed radiation through an exposed input end of the selected source fiber, and the input optical train comprises first focusing means disposed to focus the first aperture to an aperture image thereof at an image plane, and second focusing means having a focal plane located at the image plane and being disposed so that the aperture image is focused at infinity through the input end into the selected source fiber and the second focusing means focuses an input image of the second aperture onto the input end.

7. The apparatus of claim 6 further comprising an output optical train disposed with respect to the analyzer means to direct transmitted radiation from an exposed output end of the correspondingly selected return fiber, wherein the output optical train comprises an output focusing means with a configuration and a disposition with respect to the output end substantially the same as the second focusing means having a configuration and a disposition relative to the input end.

8. The apparatus of claim 6 wherein the first aperture is the source area and the second aperture is the source aperture.

9. The apparatus of claim 8 wherein the source focusing means comprises a concave mirror having a circular mirror area, the source aperture is defined by the mirror area, and the second focusing means comprises an input lens.

10. The apparatus of claim 6 wherein the input optical train further comprises an input aperture defining a size for the input image.

11. The apparatus of claim 10 wherein the input aperture is disposed at the image plane.

12. The apparatus of claim 6 wherein the fibers have common numerical aperture, and the input focusing means has a focal length cooperative with the input aperture to define an input numerical aperture substantially the same as the common numerical aperture.

13. The apparatus of claim 12 wherein each optical fiber has a core for carrying radiation, the input image has an image size, and the core has a cross sectional core size nominally mismatched from the image size.

14. The apparatus of claim 13 wherein the image size has a deviation from the core size, the deviation being between about 10% and 20% of the core size.

15. The apparatus of claim 4 wherein the retaining member has holes therethrough spaced equally on the circle coaxial with the axis, and each fiber at its exposed end is affixed in a corresponding hole.

16. The apparatus of claim 15 wherein at least one sample is a liquid for transmitting the radiation.

17. The apparatus of claim 15 wherein each pair of fibers consists of a source fiber and a return fiber having respective exposed ends located diametrically oppositely on the circle.

18. The apparatus of claim 15 wherein the positioning means comprises an axle affixed axially to the retaining member, and rotation means operatively connected to the axle for rotating the axle so as to selectively position the retaining member.

* * * * *